Figures 1A, 1B:
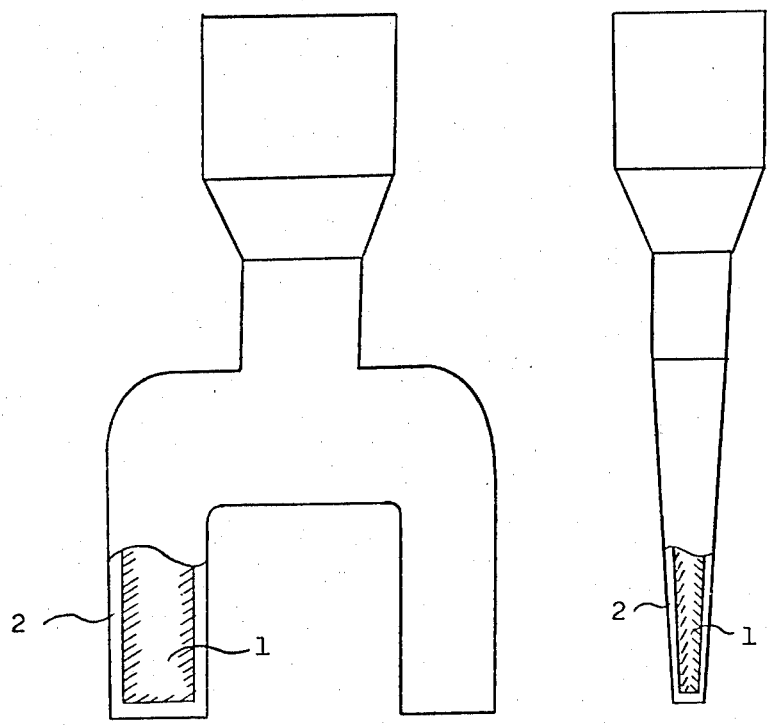

United States Patent [19]

Aoyagi et al.

[11] 4,223,412
[45] Sep. 23, 1980

[54] IMPLANTS FOR BONES, JOINTS OR TOOTH ROOTS

[75] Inventors: Masaya Aoyagi; Mikio Hayashi, both of Kawanishi; Yasuyuki Yoshida, Toyonaka; Yoshiaki Yao, Takatsuki, all of Japan

[73] Assignee: Sumitomo Chemical Company, Limited, Osaka, Japan

[21] Appl. No.: 860,958

[22] Filed: Dec. 15, 1977

[30] Foreign Application Priority Data

Dec. 16, 1976 [JP] Japan ................. 51-151725

[51] Int. Cl.³ ............ A61F 1/24; A61C 13/00; A61C 13/30
[52] U.S. Cl. .............................. 3/1.9; 3/1.91; 433/176; 433/201
[58] Field of Search ............. 3/1.9–1.913, 3/1; 128/92 C, 92 CA; 32/10 A; 433/176, 201

[56] References Cited

U.S. PATENT DOCUMENTS

| | | | |
|---|---|---|---|
| 4,051,598 | 10/1977 | Sneer | 3/1.9 X |
| 4,097,935 | 7/1978 | Jarcho | 3/1.9 |

FOREIGN PATENT DOCUMENTS 2008010 8/1971 Fed. Rep. of Germany ............ 3/1.9

OTHER PUBLICATIONS

Ceramic Implants (Paper) by L. L. Hench, Director of Biomedical Engineering, University of Florida, Gainesville, Florida, 1975, pp. 197–205.

Primary Examiner—Ronald L. Frinks
Attorney, Agent, or Firm—Birch, Stewart, Kolasch & Birch

[57] ABSTRACT

Implants for bones, joints or tooth roots having sufficient mechanical strength, excellent compatibility with living tissues and other advantageous properties can be obtained by thermally spraying a mixture of ceramics and hydroxyapatite onto a shaped core which is made of ceramics, thereby forming a coating layer of the mixture around the surface of the core.

4 Claims, 2 Drawing Figures

IMPLANTS FOR BONES, JOINTS OR TOOTH ROOTS

The present invention relates to prosthetic articles and a process for production thereof. More particularly, the invention pertains to an improved implant for bones, joints or tooth roots comprising a shaped core which is made of ceramics and coated with a thermally sprayed layer of ceramics and hydroxyapatite.

It is known that prosthetic articles, particularly such as those used as artificial bones, joints or tooth roots, must have adequate mechanical strength, and collision resistance, as well as durability. In addition, they must be compatible with living tissues and exert no harmful effect on living bodies. Various materials are used in the preparation of implants for bones, joints or tooth roots, but there has never been found any material that satisfies all of the requirements for the implants by itself.

Accordingly, many of the implants are prepared by combining two or more materials. For example, such combination implants are disclosed in German patent application (Offenlegungsschrift) No. 2,008,010. According to this German patent application, implants for bone parts or tooth parts are prepared by plasma spraying an eutectic mixture of tricalcium phosphate and tetracalcium phosphate onto a formed core having sufficient mechanical strength, said core being made of metal, ceramics or plastics, and then heating the resultant layer of the eutectic mixture at a temperature of 1,000° C. under a moist atmosphere, thereby converting the eutectic mixture into hydroxyapatite having excellent compatibility with living tissues.

As the result of a study seeking a more advantageous method for preparing implants, it has now been found that the desired implants for bones, joints or tooth roots having sufficient mechanical strength, excellent compatibility with living tissues and other advantageous properties can be obtained by thermally spraying a mixture of ceramics and hydroxyapatite onto a shaped core which is made of ceramics, thereby forming a coating layer of the mixture around the outer surface of the core.

An object of the present invention is to provide an implant for bones, joints or tooth roots comprising a shaped ceramic core coated with a thermally sprayed layer of a mixture of ceramics and hydroxyapatite.

Another object of the invention is to provide a process for preparing an implant for bones, joints or tooth roots which comprises thermally spraying a mixture of ceramics and hydroxyapatite onto a shaped ceramic core.

Further objects of the invention will be apparent from the following description.

The present invention will be hereinafter explained in detail with reference to the accompanying drawing, which is merely illustrative of an embodiment of the invention but the present invention is not limited thereto.

FIG. 1 is a partially cut-away schematic view of an embodiment of an implant for a jawbone of the blade type according to the present inveniton, wherein 1A is a front view thereof and 1B is a side view thereof, wherein 1 represents a ceramic core and 2 is a thermally sprayed layer of a mixture of ceramics and hydroxyapatite.

The ceramics used in the present invention include conventional thermal spray materials which are usually used for the treatment of the surface of metals by a thermal spray method in order to give them a corrosion resistance, wear resistance or the like. Representative thereof are metal oxides such as aluminum oxide ($Al_2O_3$), titanium oxide ($TiO_2$), zirconium oxide ($ZrO_2$), silicon dioxide ($SiO_2$), stannic oxide ($SnO_2$), phosphorus pentaoxide ($P_2O_5$), calcium oxide ($CaO$), or diboron trioxide ($B_2O_3$), which may be used alone or in the form of a mixture of two or more thereof. Among these ceramics, the particularly preferred is aluminum oxide.

The hydroxyapatite used in the present invention includes synthetic hydroxyapatite and hydroxyapatite obtained from organisms (bio-hydroxyapatite). For instance, the synthetic hydroxyapatite may be prepared by reacting $Ca_3(PO_4)_2$ with an excess amount of $CaO$ in steam at a high temperature of 900° to 1300° C. (dry synthesis) or by reacting calcium (0.5 mol/l) and an aqueous solution of phosphoric acid at a pH value of 7.1 to 7.4 and at 37° C. (wet synthesis). The bio-hydroxyapatite may be prepared by using as the starting material bones or teeth of various animals (e.g. cattle, horse, dog, chicken, rabbit, etc.), i.e. by heating the hard tissue of the bones or teeth at around 800° C. in air, dipping the resultant in a boiling liquid of ethylene diamine, whereby the organic materials contained therein are dissolved and removed off, and then burning the organic materials with oxygen, which is converted into a plasma at a low temperature, by using a low temperature ashing device.

The ceramic core of the present invention can be prepared by any one of the techniques conventionally used in preparing ceramic prosthetic articles. For example, the ceramic core having sufficient mechanical strength can be obtained by slip casting or pressing ceramics to form a particular shape, preferably with a cold isostatic press, and then baking the shaped ceramics at a temperature of 1,000° to 2,000° C. for about five hours. After or during the baking step, the ceramics core may be subjected to mechanical processing (e.g. grit blasting, griding, scoring, cutting and the like) if and when the shape of the ceramic core is a complicated one or roughness of the surface of the ceramic core is required. The shape of the ceramic core is not limited to a specific one, but may be in various forms, such as pin, screw, blade, anchor, plate, mesh, or the like. A particular shape of the ceramic core should be determined so that it fits to the receiving tissue of a host.

The layer of a mixture of ceramics and hydroxyapatite can be formed on the core by a thermal spray method (i.e. by blowing and laminating thereon the molten mixture or nearly molten by a technique of combustion or with electric energy), preferably by a plasma spray method (i.e. by applying the mixture in the form of a plasma jet of a supersonic electromagnetic fluid having a high temperature obtained by arcing). The product thus coated with the layer of the mixture may be used as the implant as it is, or may be used after baked at a temperature of 900° C. to 1300° C. in air or in a vacuum. The mixing ratio of ceramics and hydroxyapatite is not particularly limited, but they are usually mixed in a ratio of 10 to 90% by weight of hydroxyapatite and the remainder of ceramics, preferably 30 to 70% by weight of hydroxyapatite and the remainder of ceramics. The layer of the mixture is usually applied in a thickness of not more than 1000μ, preferably 100 to 300μ. The sprayed layer has a sufficient mechanical strength as well as an excellent affinity to living tissue and is firmly fixed to the ceramic core.

In addition to excellent affinity to living tissue and sufficient mechanical strength, the implant of the present invention has the following advantages:

The implant of the present invention is firmly connected with the receiving tissue of a host without the use of any bonding agent such as bone cements, since the tissue of a host grows into micropores of the thermally sprayed layer and around the uneven surface of the implant, and hydroxyapatite of the layer is absorbed into the tissue and is simultaneously replaced by the newly grown bone tissue, by which the implant is further strictly fixed to the tissue of a host.

The implant of the present invention can be applied to various parts in living bodies as an artificial bone, joint or tooth root, for instance, within teeth, bones or mucous membranes or under periostea.

The following example is given to illustrate the present invention more precisely, but it should not be interpreted to restrict the present invention thereto.

EXAMPLE

A ceramic core is prepared by the following procedure.

At first, aluminum oxide (produced by SUMITOMO CHEMICAL COMPANY,LTD., in Japan, purity: more than 99.99%, particle diameter: less than $10\mu$) is formed into a core by pressing at a pressure of 1000 kg/cm$^2$ with a cold isostatic press and subjecting the product to mechanical roughening to make the surface of the formed core uneven. Thereafter, the formed core is baked at a temperature of 1700° C. for 5 hours.

Using a plasma spray apparatus (provided with a 6MR-630 electric power supplier, made by Metco Inc.), a argonhydrogen-plasma jet flame (arc electric current: 500 amp.) is generated, and a mixture of 70% by weight of hydroxyapatite (white powder produced by the dry synthesis method, specific gravity: 3.2, particle size: not more than $100\mu$) and 30% by weight of aluminum oxide (Metco powder No. 105, made by Metco Inc.) is thermally sprayed so as to form a layer having a average thickness of about $200\mu$ on the outer surface of the ceramic core.

The implant was embedded into a tibia of a pig, and observation by a X-ray fluoroscopy was effected for 3 months. As the result, there was observed the growth of fibrous tissue around the implant. Besides, according to microscopic observation, there was observed no abnormal symptoms.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An implant comprising a shaped ceramic core having a uniform coating of a porous layer formed by plasma spraying onto the core a mixture consisting essentially of a ceramic material and hydroxyapatite, wherein said hydroxyapatite is present in an amount of 10 to 90% by weight.

2. The implant according to claim 1, wherein the shaped ceramic core is made of aluminum oxide.

3. The implant as disclosed in claim 1 wherein said porous layer is applied to a thickness of not more than 1,000 microns.

4. The implant as disclosed in claim 3 wherein said porous layer is 100 to 300 microns thick.